US00RE38590E1

(19) United States
(12) Reissued Patent
Sumiya

(10) Patent Number: US RE38,590 E
(45) Date of Reissued Patent: Sep. 14, 2004

(54) OPERATION APPARATUS FOR CORRECTING AMETROPIA WITH LASER BEAM

(75) Inventor: Toshifumi Sumiya, Nukata-gun (JP)

(73) Assignee: Nidek Co., Ltd. (JP)

( * ) Notice: This patent is subject to a terminal disclaimer.

(21) Appl. No.: 09/291,307

(22) Filed: Apr. 15, 1999

Related U.S. Patent Documents

Reissue of:
(64) Patent No.: 5,620,437
Issued: Apr. 15, 1997
Appl. No.: 08/563,005
Filed: Nov. 27, 1995

(62) Division of application No. 08/113,063, filed on Aug. 30, 1993, now Pat. No. 5,470,329.

(30) Foreign Application Priority Data

Aug. 31, 1992 (JP) ..... 4-257276

(51) Int. Cl.[7] ..... A61B 18/18; A61N 5/06
(52) U.S. Cl. ..... 606/5; 606/10; 606/11; 606/17; 351/214; 351/215; 356/132
(58) Field of Search ..... 606/3–5, 10, 12, 606/17–19; 128/898; 351/213, 214, 215; 356/132

(56) References Cited

U.S. PATENT DOCUMENTS

| | | | | |
|---|---|---|---|---|
| 4,370,540 A | | 1/1983 | Davis et al. | |
| 4,648,400 A | | 3/1987 | Schneider et al. | |
| 4,732,148 A | | 3/1988 | L'Esperance, Jr. | |
| 4,887,592 A | | 12/1989 | Loertscher | |
| 4,953,969 A | | 9/1990 | Fedorov | |
| 4,994,058 A | | 2/1991 | Raven et al. | |
| 5,147,352 A | | 9/1992 | Azema et al. | |
| 5,163,934 A | * | 11/1992 | Munnerlyn | 606/10 |
| 5,445,633 A | | 8/1995 | Nakamura et al. | |
| 5,470,329 A | * | 11/1995 | Sumiya | 606/4 |
| 5,624,436 A | * | 4/1997 | Nakamura et al. | 606/12 |
| 5,637,109 A | * | 6/1997 | Sumiya | 606/5 |

FOREIGN PATENT DOCUMENTS

| | | |
|---|---|---|
| EP | 0224322 | 3/1987 |
| EP | 0296982 | 12/1988 |
| JP | 64-86968 | 3/1989 |
| JP | 2-84955 | 3/1990 |
| JP | 4-33220 | 6/1992 |
| WO | 1019539 | 2/1991 |

* cited by examiner

*Primary Examiner*—Michael Peffley
*Assistant Examiner*—Ahmed Farah
(74) *Attorney, Agent, or Firm*—Finnegan, Henderson, Farabow, Garrett & Dunner, L.L.P.

(57) ABSTRACT

An operation apparatus for ablating the cornea by laser beam and correcting ametropia of the eye comprising a diaphragm with variable aperture, which is disposed on the optical path along which the laser beam is irradiated on the cornea, a shading member for shading the aperture of the diaphragm in the meridian diameter direction of the aperture, which is capable of varying the shading area to the aperture of the diaphragm by changing the turning angle to the optical path, in which aperture diameter of the diaphragm and variation in scope of the shading area by the shading member being controlled, and a beam rotator disposed in the eye side to the diaphragm rotates the laser beam passed through the aperture of the diaphragm about the optical path, whereby the cornea is ablated thicker at the periphery than at the center so as to correct hypermetropia.

9 Claims, 9 Drawing Sheets

PRIOR ART

OPERATION APPARATUS FOR CORRECTING AMETROPIA WITH LASER BEAM

Matter enclosed in heavy brackets [ ] appears in the original patent but forms no part of this reissue specification; matter printed in italics indicates the additions made by reissue.

This is a division of application Ser. No. 08/113,063, now U.S. Pat. No. 5,470,329 filed Aug. 30, 1993.

BACKGROUND OF THE INVENTION

1. Field of the Invention

The present invention relates to an operation apparatus for correcting ametropia of the eye by correcting the shape of a cornea with laser beam, and particularly to an operation apparatus for correcting hypermetropia by reducing the curvature of the cornea and increasing its refracting power.

2. Description of Related Art

Recently known is a method of correcting ametropia of the eye by eliminating a part from the surface of a cornea by laser beam, and thereby changing the curvature; called Photo-refractive Keratectomy. The method is currently utilized for only correction of myopia, hardly utilized for correction of hypermetropia. The reason is considered as follows.

In the case of correcting myopia, as shown in FIG. 1, the surface of the cornea $E_c$ is eliminated by laser beam so that the thickness of eliminated part is greater in the center of the cornea than in the periphery, as the eliminated part being convex lens-shaped. To eliminate the cornea as mentioned above, a regular diaphragm with variable circular aperture is utilized to change the ablation area by the laser beam on the cornea, thereby correction of myopia may be relatively easily performed.

In the case of correcting hypermetropia, contrarily, as shown in FIG. 2, the surface of a cornea $E_c$ has to be eliminated so that the thickness of eliminated part is greater in the periphery of the cornea than in the center, as the eliminated part being concave lens-shaped. Accordingly, to eliminate the surface of the cornea, an aperture diaphragm must cut laser beam to ablate the cornea off in its center part and also vary the radius size of aperture, but it is difficult for a regular diaphragm with circular aperture.

To control diaphragm utilized for correction of hypermetropia, several methods have been proposed. For instance, Japanese Patent Publication No. HEI 4(1992)-33220 based on the United Kingdom Patent Application No. GB 8606821 (Applicant: Summit Technology, Inc.,) which corresponds to U.S. Pat. No. 4,994,058, declares a method of ablating the surface of a cornea as concave lens shape with a special mask, as shown in FIG. 3. The mask provides a predefined profile of resistance to laser beam, the profile being created by varying the thickness or the composition of the mask. When laser beam is passed through the mask to irradiate the cornea, part of the laser beam is selectively absorbed and part is transmitted to the cornea in accordance with the mask profile to selectively ablate the surface. The mask for correction of hypermetropia is consisted of a center part which more absorbs and less transmits laser beam and a peripheral part which more transmits and less absorbs laser beam, so that the surface of the cornea is eliminated as concave lens shape.

Japanese Laid-Open Patent Publication No. SHO 64(1989)-86968 based on French Patent Application No. FR 8708963 corresponding to European Patent Publication No. 0 296 982 (applicant; International Business Machines Corporation) proposes another method of eliminating the surface of the cornea by laser beam, in which laser beam is irradiated to the cornea through a diaphragm with lobe-shaped aperture, while the aperture of the diaphragm being displaced in rotation or in translation over the area of the cornea to be corrected. The lobe-shaped aperture of the diaphragm is formed in a predefined shape. A plurality of the images of the lobe of the laser beam passed through the aperture of the diaphragm are intermittently formed on the cornea to eliminate the surface of a cornea by thickness necessary to correct ametropia, accordingly, the curvature of the cornea is changed according to eliminated part of the cornea. The aperture of the diaphragm utilized for correction of hypermetropia is formed in a lobe shape having large width at a part corresponding to the peripheral part of the cornea, so that the periphery of the cornea may be ablated more greatly than the center.

Another method of correcting ametropia using a diaphragm with lobe-shaped aperture, which is similar to the above Japanese Laid-Open Patent Publication No. SHO 64(1989)-86968, is described also in Japanese Laid-Open Patent Publication No. HEI 2(1990)-84955 based on U.S.S.R. Patent Application No. SU 4457772 which corresponds to U.S. Pat. No. 4,953,969.

However, in a case of correction of hypermetropia, there are following problems in the above prior methods of correcting ametropia.

In the first method using a special mask, the shape of the mask is variously required according to curvature of cornea and correction degree of refractive power of the eye to be treated, accordingly, a number of masks must be ready in various shapes for every curvature and correcting refractive power of the eye before treatment. The eliminated thickness of the cornea depending on the shape of the mask, precision of the shape of the mask is important factor in a case of correction of ametropia, and manufacture of the mask is difficult accordingly.

In the second method of displacing images of the lobe of the aperture, the shape of the aperture required is various according to curvature and correcting refractive power of the cornea to be treated, similarly as in the above method, a number of diaphragms have to be provided according to the eye to be treated.

SUMMARY OF THE INVENTION

The present invention has been made in view of the above circumstances and has an object to overcome the above problems and to provide an operation apparatus for correcting ametropia with laser beam, capable of reducing curvature of the cornea of the eye and correcting hypermetropia with simple constitution, without needing a number of masks or diaphragms.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an operation apparatus for correcting ametropia with laser beam of this invention comprises a diaphragm with variable aperture, which is disposed on the optical path along which the laser beam is irradiated on the cornea, a shading means for shading the aperture of the diaphragm in the lateral diameter direction of the aperture, capable of varying the shading area to the aperture of the diaphragm, which is disposed on the optical path, control means for controlling aperture diameter of the diaphragm and variation in scope of the shading area by the shading means, and a beam rotator for rotating the laser beam passed through the aperture of the diaphragm about the optical path, which is disposed in the eye side to the diaphragm, wherein the laser beam is rotated after passed through the diaphragm and thereby the cornea is ablated thicker at the periphery than at the center so as to correct hypermetropia.

According to the present invention, without providing a number of masks or diaphragms according to curvature and correction refractive power of the cornea to be treated, the surface of the cornea is eliminated in a concave lens shape with a simple construction, so that the curvature of the cornea can be reduced to correct hypermetropia.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of preferred embodiments of an operation apparatus for correcting ametropia with laser beam embodying the present invention will now be given referring to the accompanying drawings.

Figure 1:
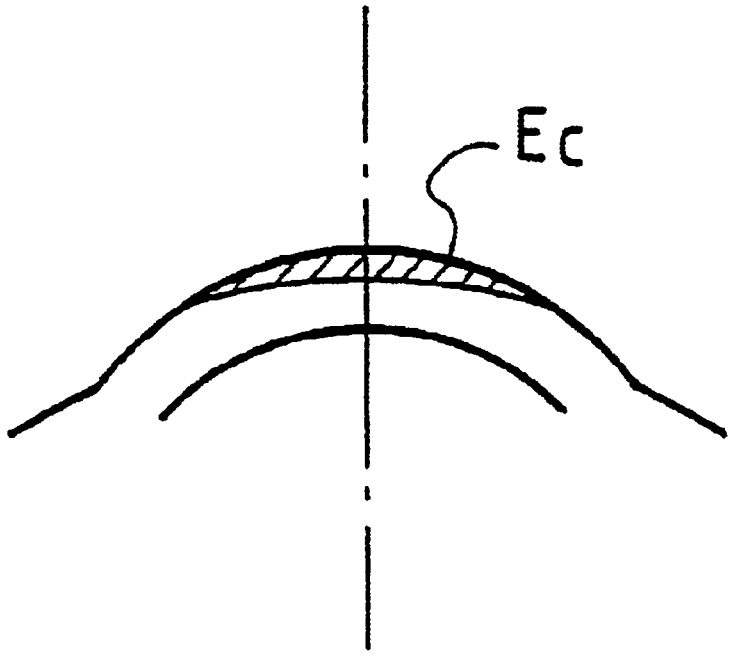
FIG. 1 is a schematic diagram of generally explaining an eliminated part of the cornea of the examinee's eye intended to correct myopia.
Figure 2:
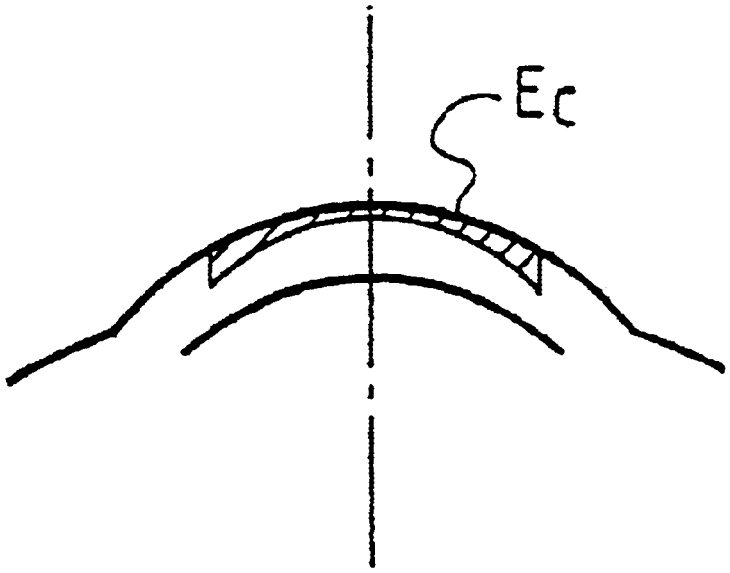
FIG. 2 is a schematic diagram of generally explaining an eliminated part of the cornea of the examinee's eye intended to correct hypermetropia.
Figure 3:
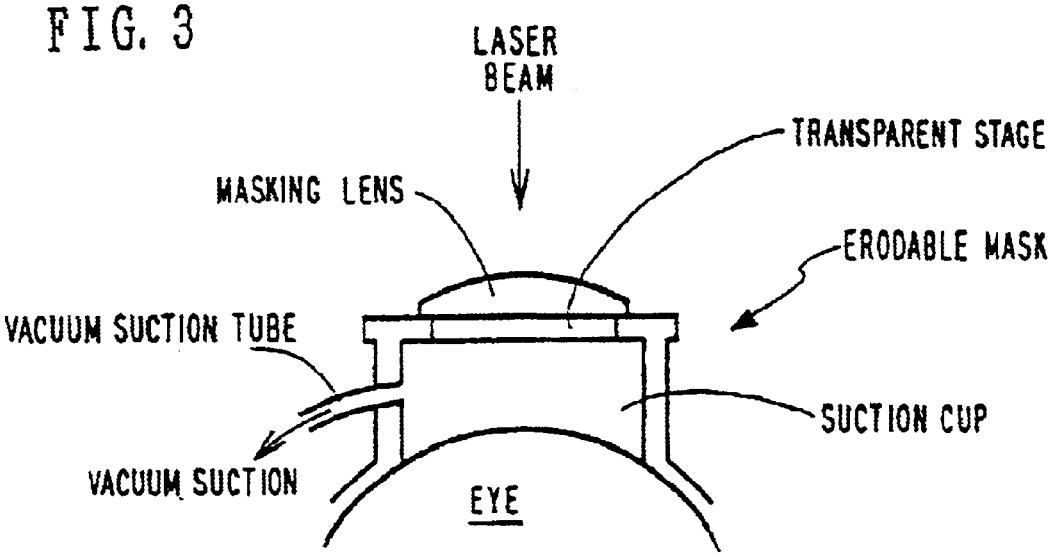
FIG. 3 is a schematic diagram of showing a prior art for eliminating the surface of the cornea with a mask to correct hypermetropia.
Figure 4:
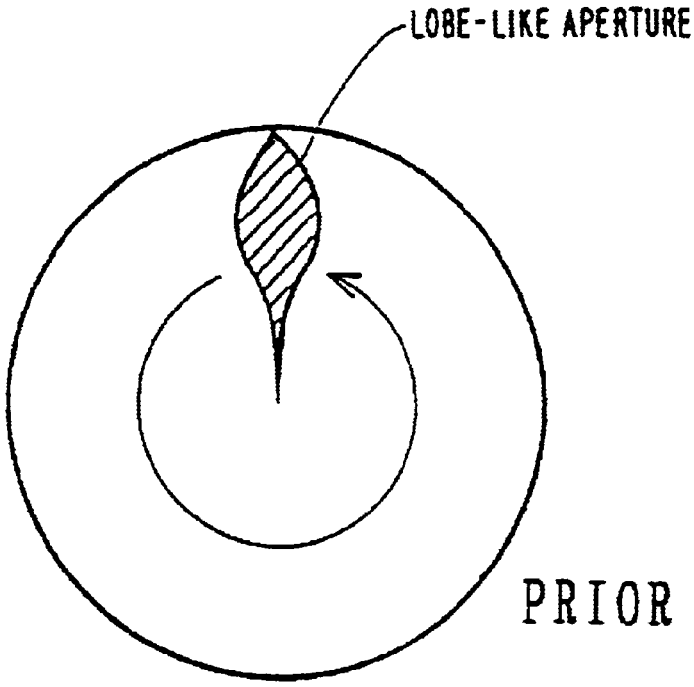
PRIOR ART FIG. 4
FIG. 4 is a schematic diagram of showing another prior art for eliminating the surface of the cornea with a diaphragm to correct hypermetropia.
Figure 5:
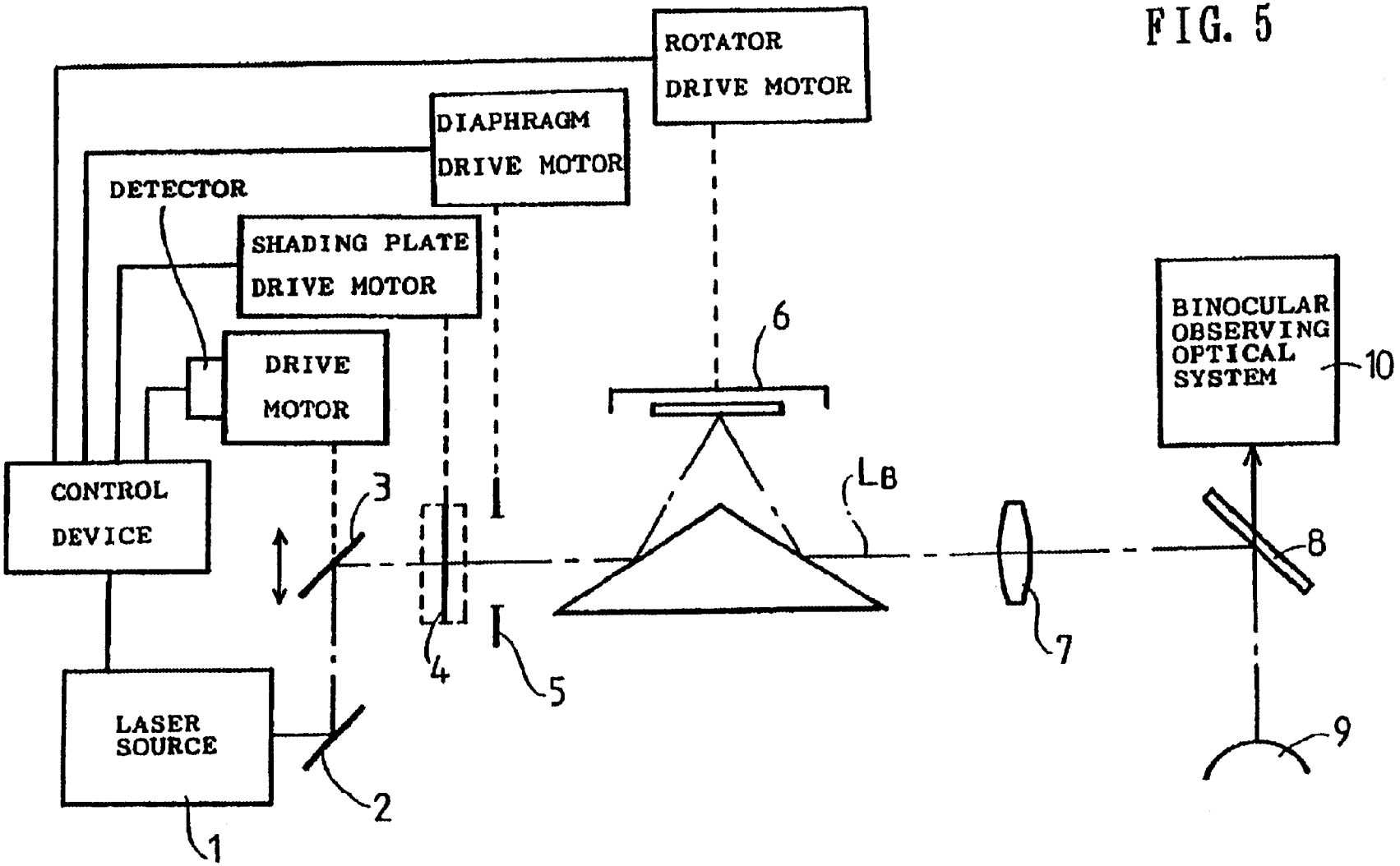
FIG. 5 is a schematic diagram of explaining the arrangement of an optical system in the first embodiment according to the present invention.

As shown in FIG. 5, an optical system of the operation apparatus includes a laser source 1 (an excimer laser source in this embodiment), plane mirrors 2 and 3 for deflecting the laser beam $L_B$ emerged from the laser source 1, an diaphragm 5 with a variable diameter located in the optical path between the mirror 3 and a projection lens 7 for projecting the laser beam $L_B$ passing through the diaphragm 5 to a cornea 9 via mirror 8.

The mirror 3 is movable parallel to the arrow shown in FIG. 5 by a drive motor, and the position of the mirror 3 (amount of movement) is detected by a positioning detector, and, on correcting myopia, the mirror 3 is moved in parallel to the arrow for irradiating the laser beam while scanning it in the direction of non-uniform intensity distribution of laser beam, thereby the cornea is ablated with an almost uniform depth. The detailed description thereof is given in Japanese Patent Appl. No. HEI 2(1990)-416767 corresponding to U.S. patent application Ser. No. 812,819 filed on Dec. 24, 1991 by the present applicant.

Image rotator 6, arranged in the above optical system between the diaphragm 5 and the projective lens 7, controls the laser beam emitted from the laser source 1 to rotate around or about the optical axis.

The laser beam $L_B$ emerged from the laser source 1 is deflected 90° by the plane mirror 2 and another 90° by the mirror 3. After the laser beam passes through the diaphragm 5 and rotated by the image rotator 6, the laser beam $L_B$ is also deflected 90° by the plane mirror 8, and projected to the surface of the cornea 9. Then, the projection lens 7 is conjugated with the diaphragm 5 and the cornea 9, and the laser beam passing through the aperture confined by a diaphragm 5 is projected on the surface of the cornea 9 so that an ablation area of the cornea is confined.

Figure 6:
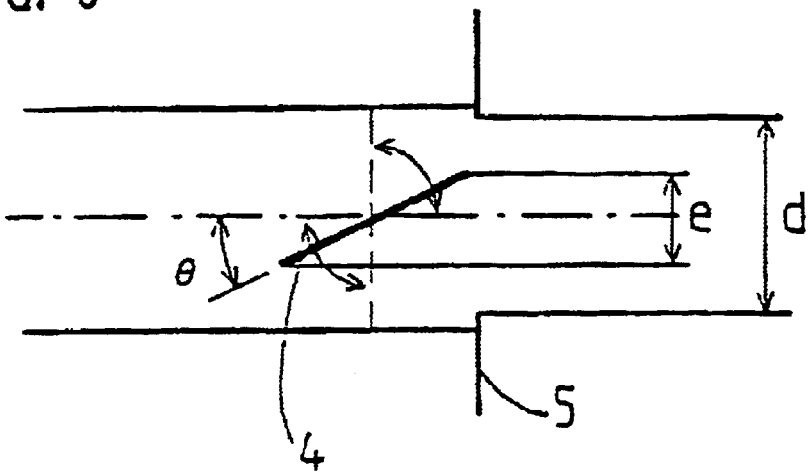
FIG. 6 is a schematic diagram of specifically explaining a constitution of a diaphragm 5 and a shading plate 4 of FIG. 5.

A shading plate 4, which is long rectangular plate, is disposed facing to the aperture of the diaphragm 5 on the optical path of the laser beam $L_B$, and, as shown in FIG. 6, capable of turning around an axis intersecting the optical path. The shading plate 4 is controlled to be displaced from the optical path on correcting myopia, and disposed on the optical path on correcting hypermetropia.

An binocular observing optical system 10, through which the image of the laser beam formed on the cornea 9 is observed, is positioned so as to put the plane mirror 8 between right and left observing optical axes of the observing optical system 10. The detail of the observing optical system has substantially no relation to the present invention, and is omitted in this specification.

Hypermetropia correcting process using the operation apparatus with the above optical system is explained as follows.

Figure 7:
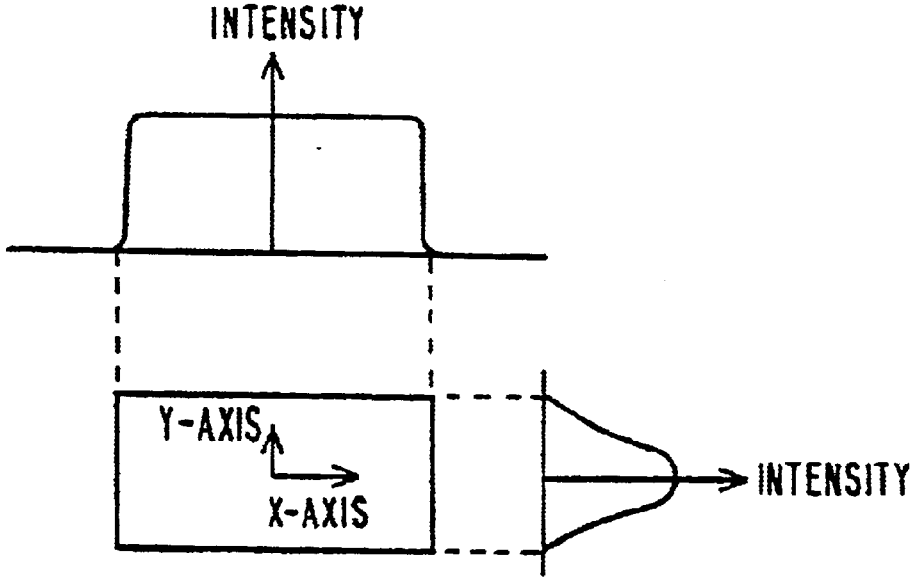
FIG. 7 is a schematic diagram of a typical form of a horizontal (X-axis) beam intensity profile and a vertical (Y-axis) beam intensity of a laser beam from an excimer laser.

The typical beam section profile of the laser beam emitted from the excimer laser source 1 is shown in FIG. 7, the laser beam has a substantial uniform intensity distribution in the horizontal direction (X-axis direction) of the laser beam, but a non-uniform beam intensity distribution in the vertical direction (Y-axis direction).

Figure 8:
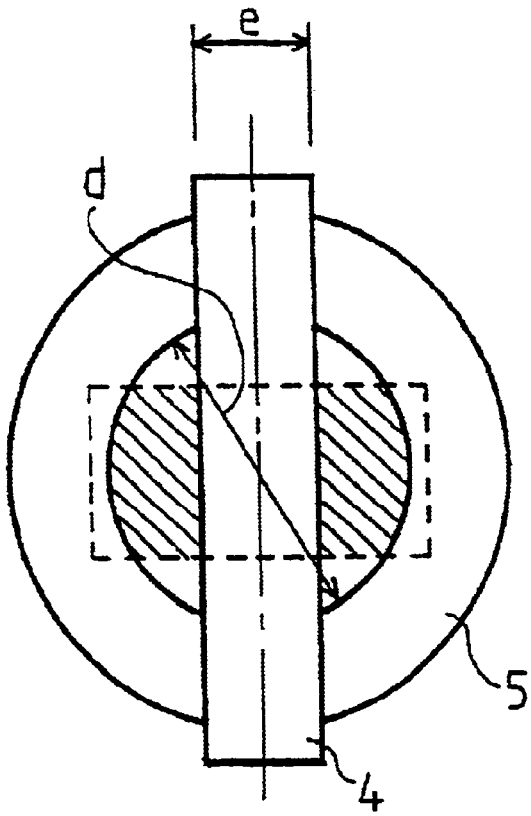
FIG. 8 is a schematic diagram of showing a long rectangular plate and a circular diaphragm taken from laser source side.
Figure 9:
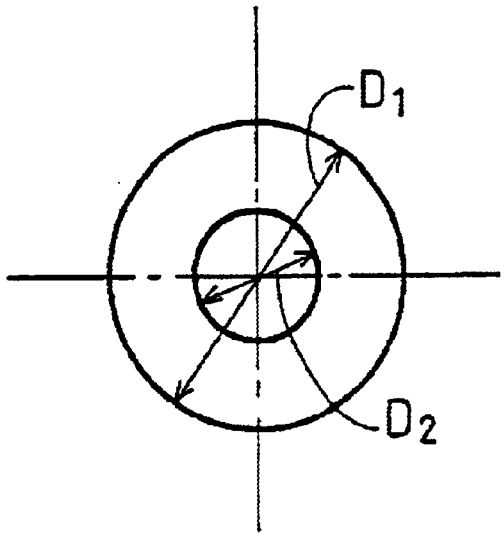
FIG. 9 is a schematic diagram of showing the ablation area in ring shape.

The diaphragm 5 and the shading plate 4 are arranged as shown in FIG. 8 taken from laser source side, so that the center part of the laser beam emitted from the laser source is cut off by the shading plate 4 and the peripheral part is cut off by the diaphragm 5, and the laser beam in only part shown with oblique lines in FIG. 8 is passed through the aperture area of the diaphragm 5 that is not shaded with the shading plate 4. The laser beam passed through the aperture of the diaphragm 5 is projected on the cornea 9 via the projection lens 7 in the shape of oblique lined part, thereby the surface of the cornea 9 is ablated. Then, the image rotator 6 disposed between the diaphragm 5 and the projection lens 7 rotates the image of the laser beam per shot to shift the ablation area on the cornea. The image rotator 6 can also be disposed between the projection lens 7 and the cornea 9. When the irradiation of laser beam is repeated by several shots, the surface of the cornea 9 is ablated in ring-shaped area as shown in FIG. 9. The outside diameter $D_1$ of the ablated area is determined according to an aperture diameter "d" of the diaphragm 5 and the magnification of the projective lens 7, and the inside diameter $D_2$ is determined according to the width "e" of the shading plate 4 (shown in FIG. 6) to cut off laser beam and the magnification of the projective lens 7.

In the above embodiment employing intact laser beam emitted from the laser source, the shading plate 4 is arranged so that both longitudinal directions of the shading plate 4 and the laser beam cross as shown in FIG. 8. And also, if the laser beam is corrected to have a uniform intensity distribution so that sectional area of the laser beam is extended, the shading plate 4 may be arranged in which direction.

Figure 10:
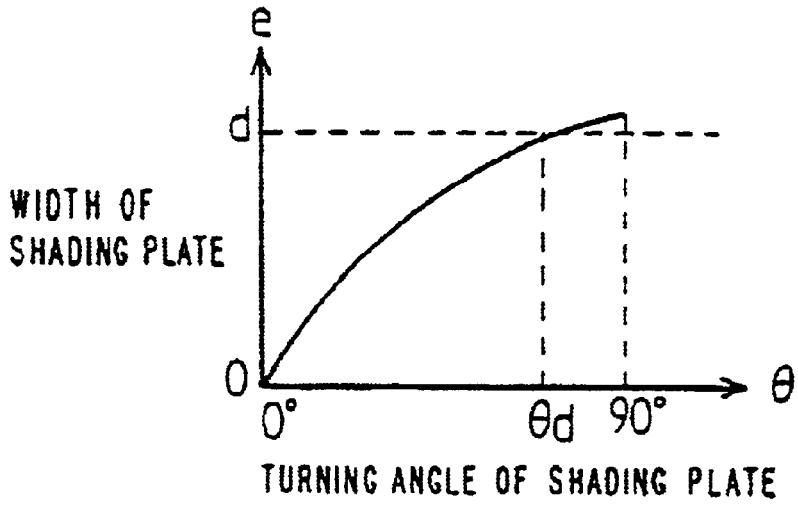
FIG. 10 is a graph showing the width of the aperture of a diaphragm according to the turning angle of the long rectangular plate.
Figure 11:
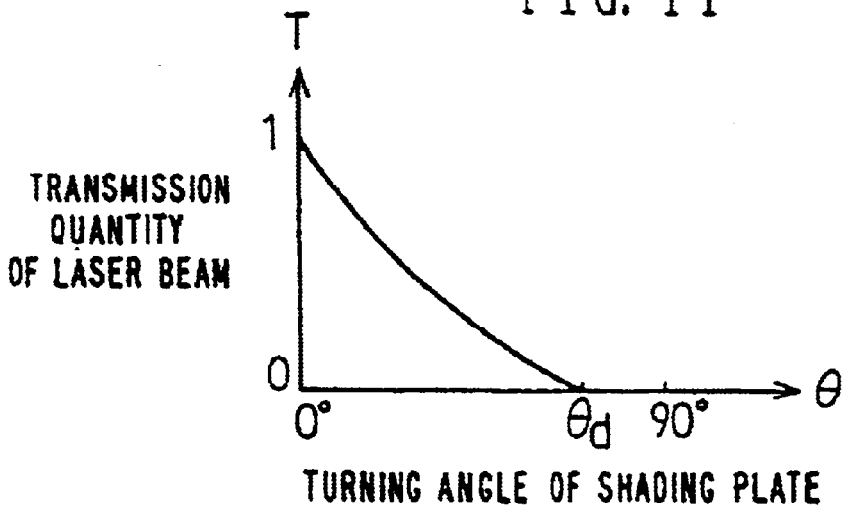
FIG. 11 is a graph showing the transmission quantity of laser beam according to the turning angle of the long rectangular plate.

The shading plate 4 being flat plate capable of turning as shown in FIGS. 6 and 8, the width "e" thereof shading the aperture of the diaphragm 5 from laser beam varies according to the turning angle "θ" as shown in FIG. 10. When the turning angle "θ" of the shading plate 4 is 0°, assuming the thickness of the shading plate 4 to be "0", the laser beam is not cut off by the shading plate 4 and all passes through the aperture of the diaphragm 5 of "d" in aperture diameter. If the transmittance of laser beam passing through the aperture of the diaphragm is "1" in the above state, the transmittance "T" of laser beam corresponding to the turning angle of the shading plate 4 is such that FIG. 11 shows. As a graph of FIG. 11, if the angle θ of the shading plate 4 increases from 0° and the width "e" of the shading plate for cutting off the laser beam extends accordingly, the ablation area on the cornea 9 is changed from the circular area with diameter $D_1$ into the ring-shaped area in which the diameter $D_2$ of the non-ablation area extending. Finally, when θ equals to $\theta_d$, the width "e" of the shading plate 4 coincides with the aperture diameter "d" of the diaphragm 5, that is, $D_2=D_1$, so that the surface of the cornea 9 is in non-ablated state.

As described above, when the shading plate 4 at angle θ to the optical axis of the laser beam is turned to change the diameter $D_2$ of the non-ablation area inside of the ring-shaped ablation area on the cornea 9, the surface of the cornea 9 is ablated slightly in its center part and deeply in its peripheral part as concave lens shape, so that hypermetropia of the eye may be corrected.

Figure 12:
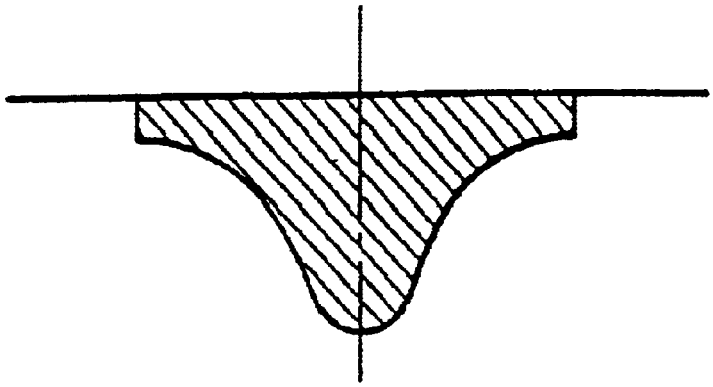
FIG. 12 is schematic diagram of showing an eliminated state by excimer laser beam rotating the laser beam having a beam intensity shown in FIG. 7.

The excimer laser beam having the intensity distribution shown in FIG. 7, if the laser beam is irradiated on the cornea while rotating just as the beam intensity distribution, the cornea is ablated more deeply in its center which corresponds to the center of the laser beam, which is a turning center of the laser beam turned by the image rotator, than in its periphery as shown in FIG. 12. Accordingly, in consideration of the above characteristic of excimer laser beam, the diameter $D_2$ of the non-ablation area according to the turning angle θ of the shading plate 4 and the rotation of the image rotator 6 have to be controlled.

Figure 14:
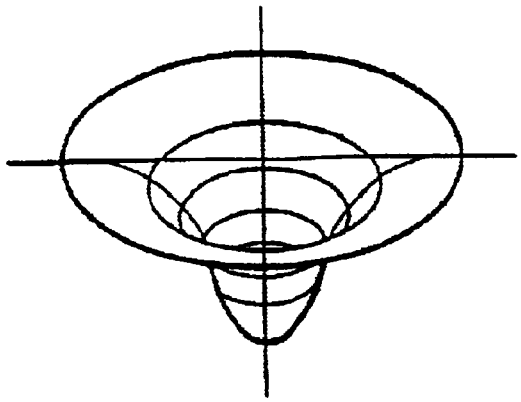
FIG. 14 is a schematic diagram of showing the rotation control to an image rotator.

More specifically, when the excimer laser beam is projected on the cornea while rotating, the image rotator 6 is controlled to rotate so that depth of ablated area of the cornea become substantially uniform in the laser beam rotating direction as shown in FIG. 14. Assuming the number of shots to be "n", which is needed for ablating the surface of the cornea by uniform thickness during one rotation of the laser beam, the image rotator is controlled to rotate at 180/n degree each so as to turn the excimer laser beam at 360/n degree each.

Figure 15:
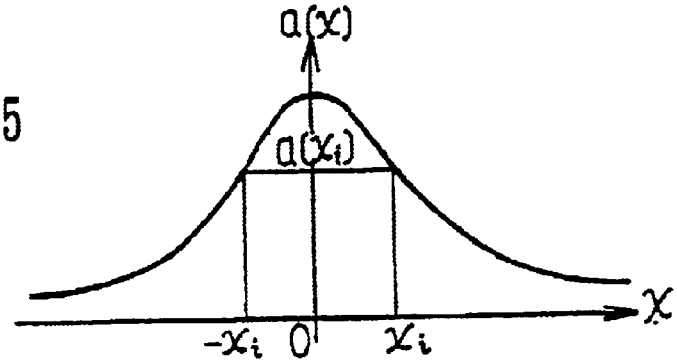
FIG. 15 is a graph of showing a relation between the rotation of an image rotator and the ablation rate.
Figure 16:
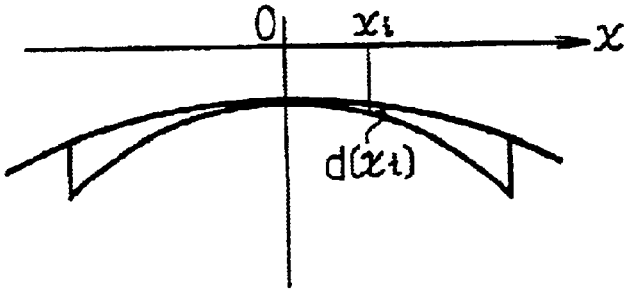
FIG. 16 is a graph of showing a relation between the depth of the eliminated part of the cornea and a distance from the center of the cornea.
Figure 17:
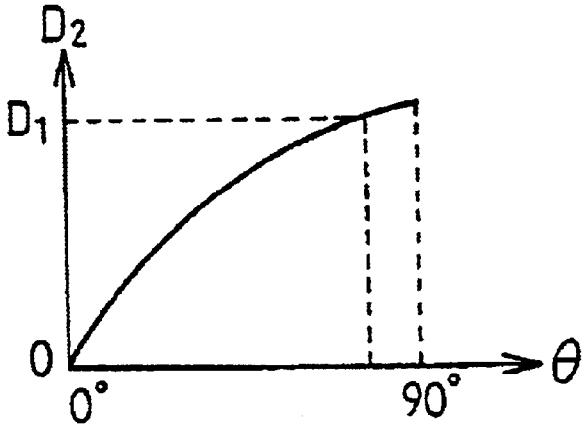
FIG. 17 is a graph of showing a relation between the turning angle θ of a shading plate and the diameter $D_2$ of non-ablation area.

If the ablation rate when the laser beam is irradiated on the cornea "n" times during one rotation is such that FIG. 15 shows, the ablation rate at a distance $x_i$ from the optical axis is indicated by $a(x_i)$. And if the cornea is eliminated as shown in FIG. 16 in correction of hypermetropia, the eliminated depth of the cornea at the distance $x_i$ is indicated by $d(x_i)$. Then, values of $x_1$, $x_2$, $x_3$ . . . when value of $d(x_i)/a(x_i)$ is 1, 2, 3 . . . are first found on the basis of the value $x_i$ multiplying from 0 step-by-step. The relation between the turning angle θ of the shading plate 4 and the diameter $D_2$ of circular non-ablated area inside the ablated area on the cornea, corresponding to the relation between the width "e" of the shading plate 4 and the diameter $D_2$ shown in FIG. 10, is plotted as shown in FIG. 17. As shown in the graph of FIG. 17, when the diameter $D_2$ is $2x_1$, $2x_2$, $2x_3$ . . . in order, the turning angle θ of the shading plate 4 is accordingly $\theta_1$, $\theta_2$, $\theta_3$ . . .

Control of the turning angle of the shading plate 4 is performed as below On the basis of the above relations.

When the turning angle of the shading plate 4 is shifted to $\theta_1$, $\theta_2$, $\theta_3$ . . . per one rotation of the laser beam by the image rotator rotating, that is, per "n" times irradiation of the laser beam, the diameter $D_2$ of the circular non-ablated area increases to $2x_1$, $2x_2$, $2x_3$ . . . accordingly. Then, part apart from the center of the cornea by distance $x_i$ is ablated repeatedly by the laser beam rotating "i" times, thereby the eliminated depth of the cornea is found by following formula:

$$a(x_i)\times i=d(x_i)$$

If the above control is repeated until $D_2$ become equal to $D_1$, the surface of the cornea is eliminated as shown in FIG. 16 so that hypermetropia of the eye can be corrected.

Figure 13:
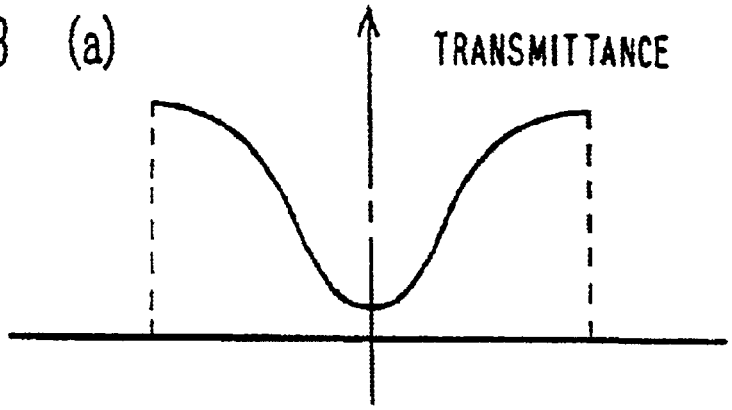
FIG. 13(a) is a diagram of showing the transmittance distribution of a filter for correcting the intensity distribution of excimer laser beam so that the eliminated state shown in FIG. 12 is in uniform depth.
FIG. 13(b) is a schematic diagram of showing a constitution where a filter 11 is disposed between a diaphragm 5 and a shading plate 4 in the embodiment.
Figure 13:
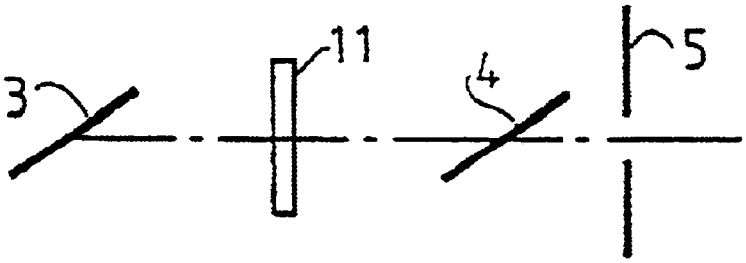

To avoid the complex control, a filter 11, having transmittance distribution shown in FIG. 13(a), may be disposed on the optical path between the laser source 1 and the shading plate 4 as shown in FIG. 13(b), so that the beam intensity distribution of the laser beam is corrected to be uniform through the filter 11.

In the above embodiment, although the shading plate 4 is turned to change the width "e" thereof, another method can be used for changing the width "e" to cut off the laser beam.

Figure 18:
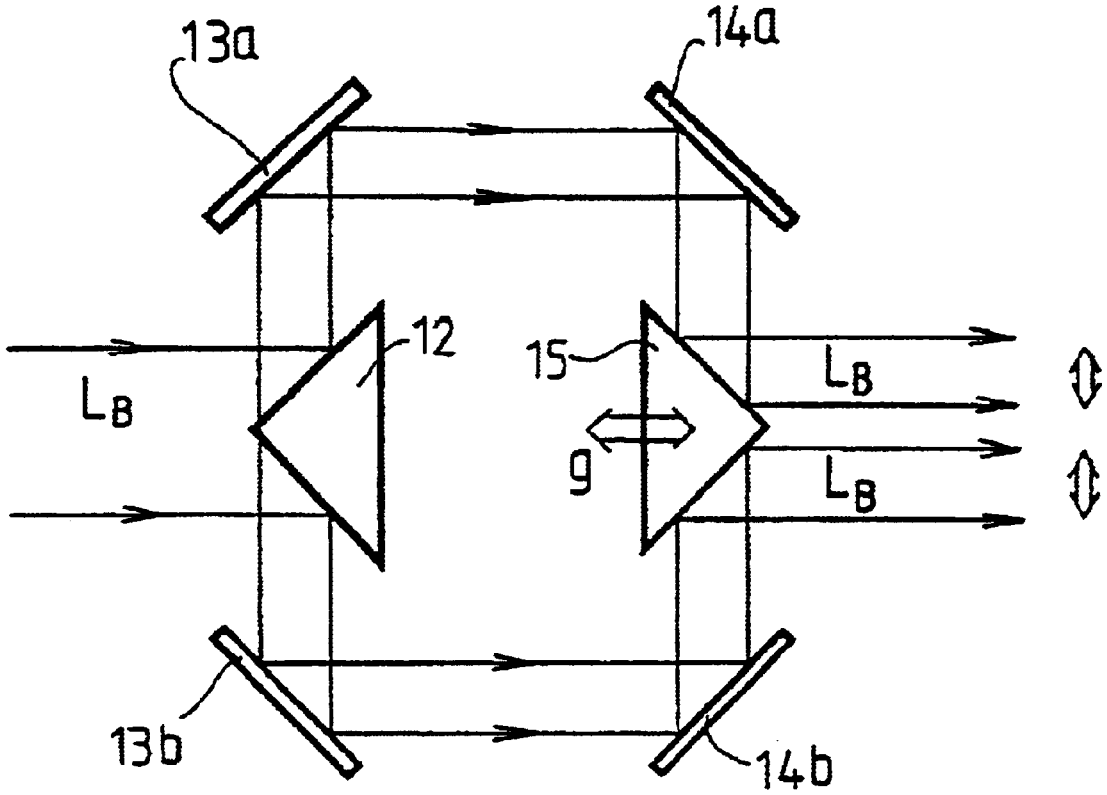
FIG. 18 is a schematic diagram of explaining a component of controlling the ablation area by laser beam through the optical system which includes a plurality of mirrors and prisms in another embodiment according to the present invention.

Further, the center part of the laser beam can be cut off by a plurality of mirrors instead of the shading plate 4, the mirrors which divide laser beam into two beams and leaves a space between the two beams. As shown in FIG. 18, specifically, the laser beam emitted from the laser source is divided into two beams by a triangle prism 12 disposed on the optical path of the laser beam, and deflected by mirrors 13a, 14a disposed on one optical path of the divided laser beams and mirrors 13b, 14b disposed on another optical path onto a triangle prism 15. The prism 15 is movable in parallel to the arrow "g" of FIG. 18. The laser beams deflected on the prism 15 are projected on the cornea to ablate its surface, then the prism 15 is moved so that the non-ablation area on the cornea is adjusted to have the designated diameter, so that the cornea is ablated thinly in the center part and thick toward the periphery to correct hypermetropia.

The operation of the present apparatus, for instance to drive the driving unit including drive motors, is controlled by a microcomputer of the control device. The detailed explanation thereof is omitted in this specification.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for ablating the cornea of an eye by a laser beam of ultraviolet rays to correct hypermetropia of the eye, comprising:

a laser source for emitting a laser beam;

[a] *an* optical system for reflecting and directing the laser beam onto a cornea;

a diaphragm for restricting an irradiation area within a circle area about an apex of the cornea, disposed in an optical path of the optical system;

irradiation area restricting means having a beam shading boundary line intersecting the meridian of the cornea at right angles, disposed in the optical path of the optical system, the means restricting the irradiation area of the laser beam with the irradiation boundary line intersecting the meridian of the cornea in cooperation with the diaphragm and changing a distance from the apex of the cornea to the irradiation boundary line;

beam rotating means for rotating the irradiation area of the laser beam formed by the diaphragm and the irradiation area restricting means about the apex of the cornea, the beam rotating means being controlled to cover all meridians of the cornea and to be in a same depth at a position of the same radius as one cycle of the irradiation of the laser beam; and control means for controlling the laser source, the irradiation area restricting means and the beam rotating means to provide a first small amount of irradiation at a central portion of the cornea and to provide a second amount of irradiation larger than said first amount around a peripheral portion thereof, so that the curvature of the cornea's optical zone is made larger than before the cornea is ablated.

2. The apparatus according to claim 1, wherein the laser source comprises an [argon-fluorine] *argon-fluoride* excimer laser oscillator.

3. The apparatus according to claim 1, wherein the beam rotating means comprises an image rotator for rotating the laser beam, disposed in a down stream against the diaphragm and the irradiation area restricting means.

*4. An apparatus for use in ablating a cornea of an eye by a laser beam emitted from a laser source and passed along an optical path onto the cornea to correct ametropia of the eye comprising:*

*a diaphragm with a variable diameter aperture disposed in the optical path along which the laser beam is passed onto the cornea;*

*a movable shading element disposed in the optical path which shades a portion of the aperture of the diaphragm and which varies a width of the shaded portion of the aperture when moved, said shaded portion extending along a meridian diameter of the aperture;*

*a controller connected to the diaphragm and the shading element which controls the aperture diameter and moves the shading element to vary the width of the shaded area;*

*a beam rotator for rotating the resulting laser beam about the optical path and on the cornea; and*

*a control device which controls the beam rotator to rotate the laser beam on the cornea so that the depth of an area of the cornea ablated by the laser beam is substantially uniform in the laser beam rotating direction when the beam rotator has rotated the laser beam 360°, whereby the cornea can be ablated more at its periphery than at its center so as to correct hypermetropia.*

*5. An apparatus for ablating a cornea by a laser beam and for correcting ametropia, comprising:*

*a laser source for emitting the laser beam along an optical path;*

*a diaphragm with a variable diameter aperture, disposed in the optical path of the laser beam;*

*a movable shading element which shades a portion of the aperture extending along a meridian diameter of the aperture and which varies a width of the shaded area of the aperture when moved;*

*a controller connected to the diaphragm and the shading element for controlling the aperture diameter and moving the shading element to vary the width of the shaded area;*

*a beam rotator for rotating the resulting laser beam about the optical path and on the cornea; and*

*a control device which controls the beam rotator to rotate the laser beam on the cornea so that the depth of an area of the cornea ablated by the laser beam is substantially uniform in the laser beam rotating direction when the beam rotator has rotated the laser beam 360°, whereby the cornea can be ablated more at its periphery than at its center so as to correct hypermetropia.*

*6. An apparatus for use in ablating a cornea of an eye by a laser beam emitted from a laser source and passed along an optical path onto the cornea to correct ametropia of the eye, comprising:*

*a diaphragm with a variable diameter aperture disposed in the optical path along which the laser beam is passed onto the cornea;*

*a movable shading plate disposed in the optical path for shading a portion of the aperture of the diaphragm extending along a meridian diameter of the aperture and varying a width of the shaded area of the aperture when moved;*

*a controller connected to the diaphragm and the shading plate which controls the aperture diameter and moves the shading plate to vary the width of the shaded area;*

*a beam rotator for rotating the resulting laser beam about the optical path and on the cornea; and*

*a control device which controls the beam rotator to rotate the laser beam on the cornea so that the depth of an area of the cornea ablated by the laser beam is substantially uniform in the laser beam rotating direction when the beam rotator has rotated the laser beam 360°, whereby the cornea can be ablated more at its periphery than at its center so as to correct hypermetropia.*

*7. An apparatus for ablating a cornea by a laser beam and for correcting ametropia, comprising:*

*a laser source for emitting the laser beam along an optical path;*

*a diaphragm with a variable diameter aperture, disposed in the optical path of the laser beam;*

*a movable shading plate which shades a portion of the aperture extending along a meridian diameter of the aperture and which varies a width of the shaded area of the aperture when moved;*

*a controller connected to the diaphragm and the shading plate for controlling the aperture diameter and moving the shading plate to vary the width of the shaded area;*

*a beam rotator for rotating the resulting laser beam about the optical path and on the cornea; and*

*a control device which controls the beam rotator to rotate the laser beam on the cornea so that the depth of an area of the cornea ablated by the laser beam is substantially uniform in the laser beam rotating direction when the beam rotator has rotated the laser beam 360°, whereby the cornea can be ablated more at its periphery than at is center so as to correct hypermetropia.*

*8. An apparatus for ablating a cornea of an eye by a laser beam of ultraviolet rays to correct hypermetropia of the eye, comprising:*

*a laser source for emitting a laser beam;*

*an optical system for reflecting and directing the laser beam onto a cornea;*

*a diaphragm for restricting an irradiation area within a circle area about an apex of the cornea, disposed in an optical path of the optical system;*

*an irradiation area restricting element having a beam shading boundary line intersecting the meridian of the cornea at right angles and being disposed in the optical path of the optical system, when the irradiation area restricting element operates in cooperation with the diaphragm to change a distance from the apex of the cornea to the irradiation boundary line;*

*a beam rotator which rotates the irradiation area of the laser beam about the apex of the cornea; and*

*a controller which controls the laser source, the irradiation area restricting element and the beam rotator so as to increase the curvature of the cornea.*

*9. An apparatus for ablating a cornea of an eye by a laser beam of ultraviolet rays to correct hypermetropia of the eye, comprising:*

*a laser source for emitting a laser beam;*

*an optical system for reflecting and directing the laser beam onto a cornea;*

*a diaphragm for restricting an irradiation area within a circle area about an apex of the cornea, disposed in an optical path of the optical system;*

*an irradiating area restricting plate having a beam shading boundary line intersecting the meridian of the cornea at right angles and being disposed in the optical path of the optical system, wherein the irradiation area restricting plate operates in cooperation with the diaphragm to change a distance from the apex of the cornea to the irradiation boundary line;*

*a beam rotator which rotates the irradiation area of the laser beam about the apex of the cornea; and*

*a controller which controls the laser source, the irradiation area restricting plate and the beam rotator so as to increase the curvature of the cornea.*

* * * * *